United States Patent [19]

Ford et al.

[11] 3,982,542
[45] Sept. 28, 1976

[54] ELECTRORESECTROSCOPE AND METHOD OF LAPAROSCOPIC TUBAL STERILIZATION

[76] Inventors: John L. Ford, 4651 E. Palomino Road; John Serafin, 4120 E. Earll Drive, both of Phoenix, Ariz. 85018

[22] Filed: Mar. 12, 1975

[21] Appl. No.: 557,469

[52] U.S. Cl. ............... 128/303.14; 128/303.17
[51] Int. Cl.² ............................................ A61B 17/38
[58] Field of Search ............... 128/303.13–303.18, 128/407–409, 4

[56] References Cited
UNITED STATES PATENTS

| | | | |
|---|---|---|---|
| 1,731,069 | 10/1929 | Herman | 128/303.16 |
| 2,034,785 | 3/1936 | Wappler | 128/303.15 |
| 3,805,791 | 4/1974 | Seuberth | 128/303.14 |
| 3,831,607 | 8/1974 | Lindemann | 128/303.17 |
| 3,834,392 | 9/1974 | Lampman | 128/303.13 |
| 3,870,048 | 3/1975 | Yoon | 128/4 |
| 3,938,527 | 2/1976 | Rioux et al. | 128/303.17 |

*Primary Examiner*—Robert W. Michell
*Assistant Examiner*—Lee S. Cohen
*Attorney, Agent, or Firm*—Don J. Flickinger

[57] ABSTRACT

An elongate stylet slidably disposed within a thermoelectric insulative sheath has a forward-projecting surgically incisive tip for entry of the sheath into the peritoneal cavity. After the stylet is withdrawn, an elongate shaft having hook-shaped electrical resistance element extending forwardly therefrom is slidably inserted through the sheath and the resistance element engaged with a Fallopian tube. Subsequently, the sheath is moved forwardly to encase the resistance element in the doubled section of Fallopian tube engaged therewith. An electrical energy impulse from a controlled source thereof energizes the resistance element for concurrent electroresection and electrocoagulation of the Fallopian tube in an environment shielded from adjacent organs.

5 Claims, 6 Drawing Figures

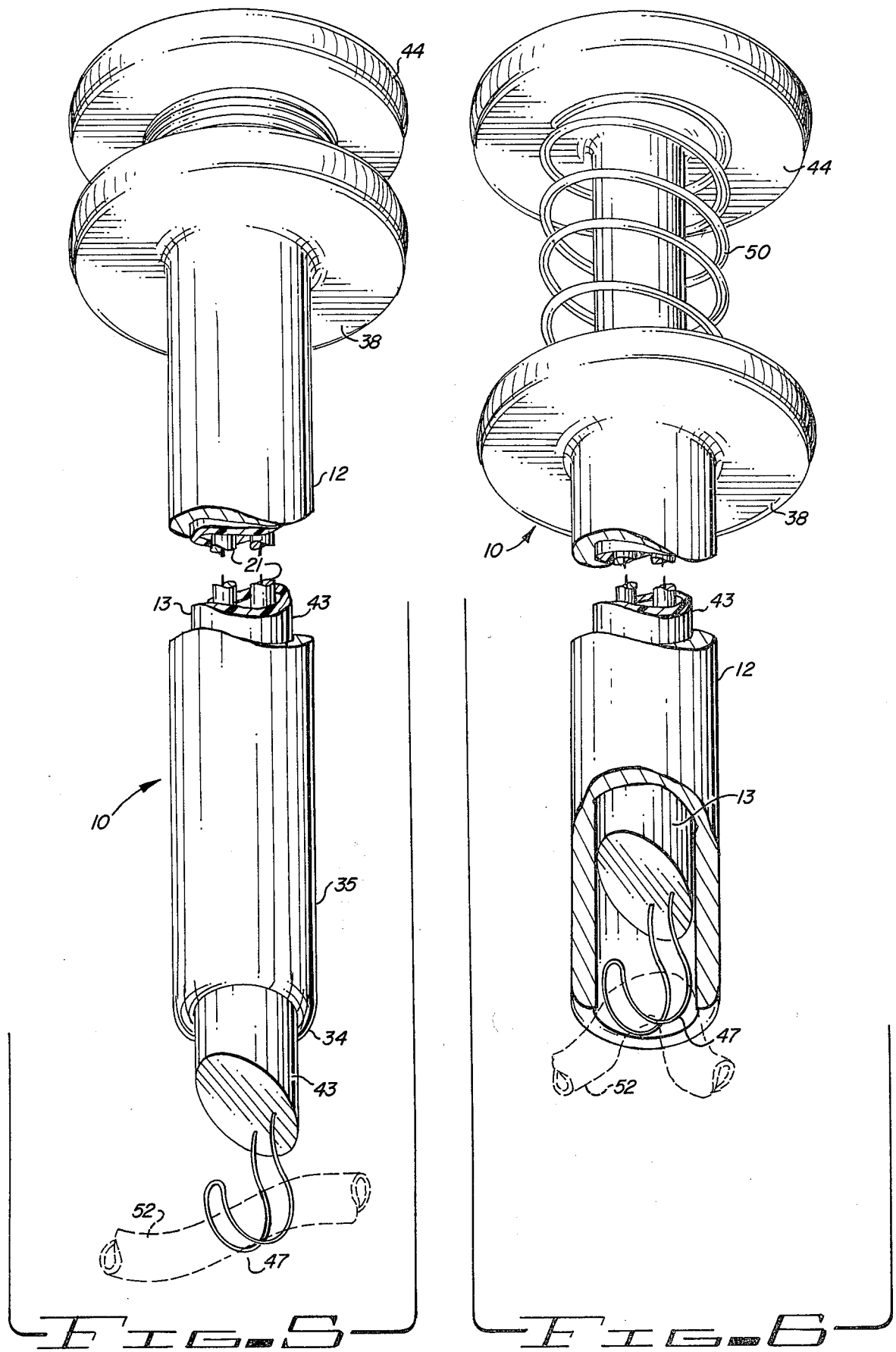

ELECTRORESECTROSCOPE AND METHOD OF LAPAROSCOPIC TUBAL STERILIZATION

This invention relates to surgical instruments.

More specifically, the invention relates to an electrically energized resectroscope.

In a further aspect, the instant invention concerns an electroresectroscope for laparoscopic tubal sterilization.

During the past several years, beginning in the latter part of the previous decade, laparoscopy has become one of the more commonly performed gynecologic procedures. As a direct result, laparoscopic tubal sterilization is now widely accepted as the standard method of female sterilization.

The procedural mechanics are relatively simple. After the patient is anesthesized, a cannula is inserted through the abdominal wall for insufflation of the peritoneal cavity. A laparoscope, through which the surgeon views the procedure, is introduced into the peritoneal cavity. The tubal sterilization is then accomplished by electroresection. Conventionally, the electroresection is accomplished through a small opening provided by a trocar and generally consists of electrocoagulating a section of the Fallopian tube and subsequently severing the tube within the coagulated area to produce a separation of fulgurated ends.

Substantial medical activity and effort have been directed to the development of laparoscopic tubal sterilization and reducing complications associated therewith. The effort includes perfecting the surgical procedure and the production of advanced laparoscopic instruments.

Regardless of the advance of medical procedures and the inherent mechanical simplicity of the operation, complications frequently arise during a laparoscopic tubal sterilization. The majority of complications are in connection with the performance of the tubal electrosurgery. During electrosurgery, the patient and the surgeon are potentially subjected to electrosurgical burns. During surgery, the coagulating tip is the active electrode which concentrates the current at the point of application. The active electrode is manually controlled by the surgeon. The circuit is completed by a disbursive electrode or ground plate in broad contact with the skin. The current is therefore caused to pass through the patient from the point of operation to the ground plate. If the ground is inadequate or defective, the current will flow through any available low-resistance path. High voltage/high frequency electricity is not infrequently responsible for abdominal wall burns and perferating the bowel.

During electrosurgery, the coagulating electrode is in close proximity to surrounding tissues and other operative instruments. It is not uncommon for the coagulating tip to obliterate the blood supply to the ovary. This is thought to be the cause of menstrual problems and early menopause in young females. Surgeons have reported facial burns when the tip of the laparoscope inadvertently short-circuited against the active electrode.

Record is made of pregnancy subsequent to laparoscopic tubal sterilization in which the Fallopian tubes were coagulated, but not resected.

In view of the foregoing discussion, it would be highly advantageous to reduce complications associated with laparoscopic tubal sterilization.

Accordingly, it is a principal object of the present invention to provide an improved method of performing a laparoscopic tubal sterilization and an improved surgical kit including instruments for use therewith.

Another object of the instant invention is the provision of a resectroscope for simultaneous elecctroresection ad electrocoagulation of a Fallopian tube. electroresection still another object of the invention is the electrosurgery of specified tissue in a shielded environment for the prevention of thermal burns to adjacent organs.

Yet another object of the invention is the performance of electrosurgical tubal sterilization in which the isolated operative tissue is subjected to a localized electrical current.

Yet still a further object of the present invention is the simplification of the laparoscopic tubal sterilization procedure, while reducing the complications heretofore associated therewith.

Briefly, to achieve the desired objectives of the present invention, first provided is a trocar comprising an elongate sheath and a first elongate stylet having a surgically incisive tip slidably received through the sheath. The surgically incisive tip provides an incision for entry of the trocar into the abdominal cavity and placement of the forward end of the sheath in the surgical area. Also provided is a second stylet similarly slidably received within the sheath and having an elongate shaft with a hook-shaped electrical resistance heating element extending from the forward end thereof. Means are provided for transmitting a controlled predetermined electrical energy impulse to the heating element.

After the sheath is positioned as above described, the first stylet is withdrawn and the second stylet inserted until the heating element extends beyond the forward end of the sheath. A Fallopian tube is engaged by the hook-shaped heating element. Rearward movement of the second stylet relative the sheath retracts the resistance element and a portion of doubled Fallopian tube engaged therewith within the thermoelectric insulating end of the tubular sheath. Applying electrical energy to the resistance element simultaneously coagulates and severs the Fallopian tube within a shielded environment.

The foregoing and further and more specific objects and advantages of the present invention will become immediately apparent to those skilled in the art from the following detailed description thereof, taken in conjunction with the drawings, in which:

FIG. 5 is a fragmentary perspective view of the electroscope of FIG. 3 as it would appear when first engaging a Fallopian tube; and FIG. 6 is a fragmentary perspective view, partly broken away, illustrating the resectroscope as it would appear during a subsequent stage of the operation.

Figure 1:
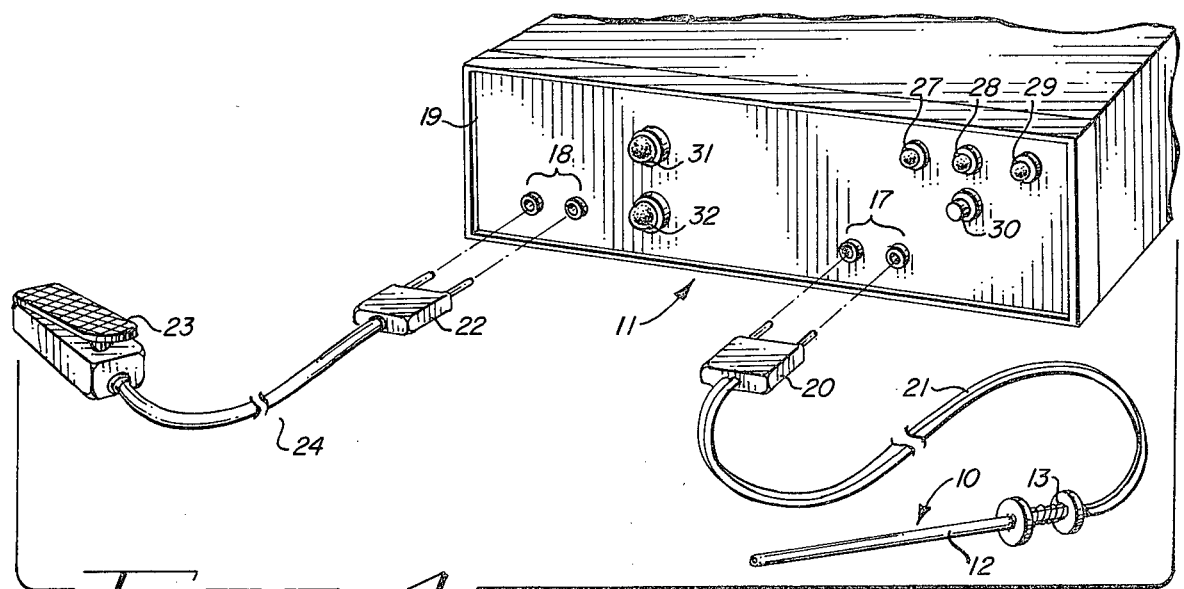
FIG. 1 is a partial perspective view of a resectroscope apparatus constructed in accordance with the teachings of the present invention.

Turning now to the drawings, in which the same reference numerals indicate corresponding elements throughout the several views, attention is first directed to FIG. 1, which shows the resectroscope, generally designated by the reference character 10, and a power supply, generally designated by the reference character 11, for providing a predetermined electrical energy impulse thereto. The resectroscope 10 includes an elongate tubular sheath 12 and an elongate stylet 13 slidably received therein, as will be hereinafter described in detail.

The power supply 11, in accordance with a preferred embodiment thereof, utilizes a nickel-chrome gel battery to provide an electrical output of 6 volts direct current at 10 amperes. Two pair of female receptacles 17 and 18 are arranged upon the face 19 of power supply 11. Male connector 20 is immovably received within receptacles 17 for transmission of electrical current through leads 21 to energize resectroscope 10. Male connector 22 is slidably received in receptacles 18 for activation of power supply 11 by foot switch 23 through leads 24. Test lights 27, 28 and 29 indicate the condition of the battery. In accordance with standard practice, the lights 27, 28 and 29 are colored, respectively, green, yellow and red and indicate, respectively, that the battery is sufficiently charged, low or depleted. The appropriate light responds when momentary contact switch 30 is depressed. Lights 31 and 32 are associated with the operational mode of the unit and may indicate, respectively, operating or charging.

Circuitry and construction details of the d-c power supply 11 as above described will be immediately apparent to those skilled in the art and readily fabricated by those having an appreciation for the requirements thereof in accordance with the present invention. In this respect, it is particularly noted that the power supply 11 includes a timing mechanism which is reset and activated by foot switch 23 to provide an electrical impulse of predetermined duration to resectroscope 10. Extensive experimentation has revealed that a duration of approximately 20 seconds is optimum for performance of the operation. The d-c power supply 11, as described, provides a completely portable electrosurgical device. However, it will be appreciated and readily apparent to those skilled in the electronic art that the battery may be discarded in favor of additional circuitry for direct connection to a readily available source of alternating current.

Figure 2:
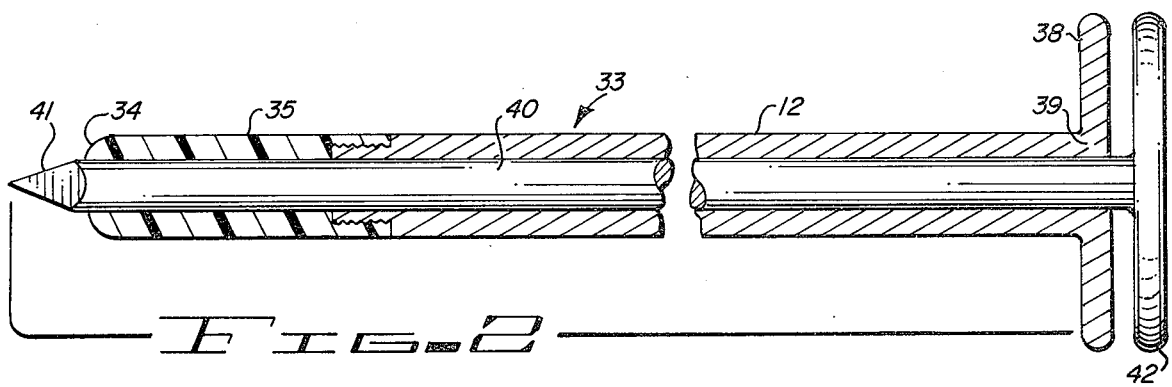
FIG. 2 is a vertical sectional view of a trocar for use in connection with the apparatus of FIG. 1.

Specifically seen in FIG. 2 is a trocar, generally designated by the reference character 33, which includes elongate tubular sheath 12. Although sheath 12 may be variously fabricated of differing materials and sizes, a stainless steel sheath approximately 8 mm. in diameter by 16½ cm. long is preferred. Sheath 12 has a forward probe end 34 which includes a disposable thermoelectric insulating tip 35, as might be inexpensively fabricated from teflon, and removably threadedly engaged with the main portion of the sheath. An outwardly directed radial flange 38 at the rearward end 39 of sheath 12 provides a fingergrasp under which the surgeon may engage his index and middle fingers. An elongate stylet 40, having a surgically incisive tip 41 at the forward end thereof and a disk-like pad 42 at the rearward end thereof, is slidably received within tubular sheath 12. Pad 42 provides a thumbrest to assist the surgeon in manipulating trocar 33. It is noted that incisive tip 41 extends beyond the forward end 34 of sheath 12 when stylet 40 is fully inserted therein.

Figure 3:
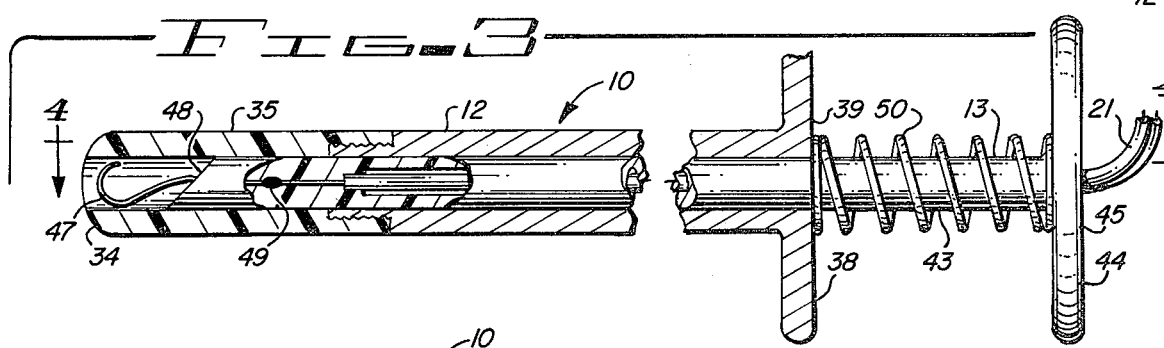
FIG. 3 is an elevational view, partly in section, of the resectroscope of FIG. 1.
Figure 4:
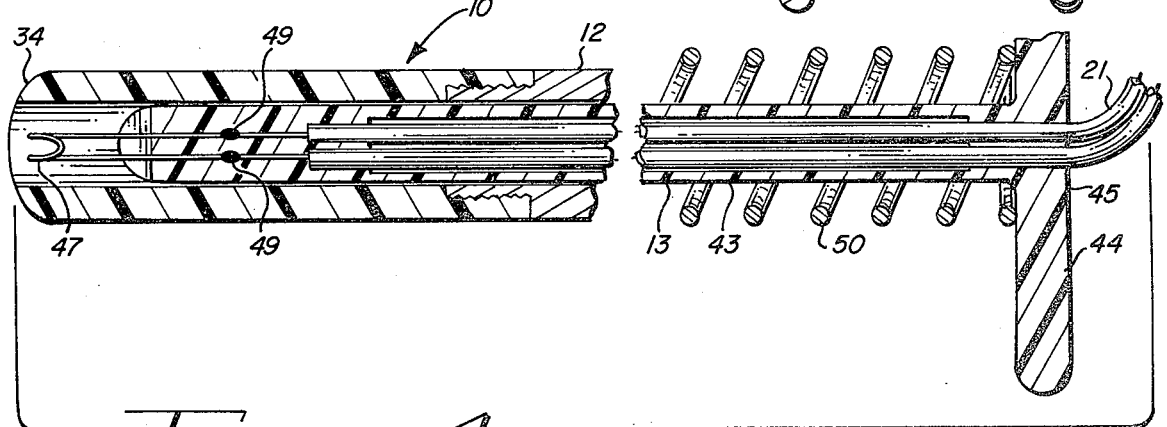
FIG. 4 is a slightly enlarged horizontal sectional view of the device of FIG. 3, taken along the line 4—4 thereof.

FIGS. 3 and 4 further illustrate resectroscope 10 which utilizes sheath 12 in common with trocar 33.

Stylet 13 includes an elongate shaft 43 slidably received within tubular sheath 12 and having a flange 44 at the rearward end 45 thereof to provide a fingergrasp or thumb pad. Heating element 47 extends from the forward end 48 of elongate shaft 43. Heating element 47 is a loop of resistance wire formed into a hook. In accordance with the output of the power supply 11, a hook-shaped heating element fashioned from 0.015 inch diameter chromel wire or the equivalent thereof provides the correct resistance. Electric leads 21 are connected to the resistance wire as shown at 49. The insulative covering of electric leads 21 extends through tube 43 nearly to connection 49. Further insulation is provided by fabricating stylet 13 from a non-conductor, such as nylon. The stylet 13 may be alternately fabricated of metal and incorporate an insulative tip to receive the ends of resistance wire 47 in the exposed portions of electric leads 21. Elongate shaft 13 is longer than sheath 12 such that hook-shaped resistance element 47 may extend beyond the forward end 34 thereof. Compression spring 50, bearing against the rearward end 39 of sheath 12, urges stylet 13 rearward relative sheath 12 to a normal resting position wherein electric element 47 is fully encased within insulative end 35.

The performance of a laparoscopic tubal sterilization is best described with reference to FIGS. 5 and 6. After insufflation of the peritoneal cavity and introduction of the laparoscope, in accordance with standard medical procedure, trocar 33 is inserted through the abdominal wall. Tip 41 provides an incision for passage of the sheath 12 through the abdominal wall with tip 34 directed to the surgical area. Stylet 40 is then withdrawn from sheath 12.

With sheath 12 in place, stylet 13 is slidably inserted therein. As particularly seen in FIG. 5, shaft 43 of stylet 13 is longer than sheath 12 and as spring 50 is compressed, the hook-shaped electrical resistance element 47 extends beyond the forward end 34 of sheath 12. Electroresectroscope 10 is manipulated with heating element 47 held in the extended position until Fallopian tube, represented by dashed outline 52, is engaged by hook-shaped element 47. During the foregoing manipulation of electroresectroscope 10, the surgeon normally engages the index finger and middle finger under flange 38 and rests thumb upon disk-like pad 44 in a manner analogous to using a hypodermic needle.

When the surgeon's grip is relaxed, compression spring 50 expands, retracting the resistance element 47 and the doubled portion of Fallopian tube 52 engaged thereby within the insulative section 35 of tubular sheath 12. With resistance element 47 and the section of Fallopian tube 52 to be resected and coagulated thermoelectrically isolated from surrounding organs and tissues, foot switch 23 is depressed, applying electrical energy to resistance element 47. The heat produced as the electrical energy impulse passes through resistance element 47 removes a small section of Fallopian tube 52, coagulating the tube at either end of the resection to produce two fulgurated ends. In accordance with the construction of electroresectroscope 10, as previously described, resistance element 47 is a closed circuit and the electrical energy supplied thereto is localized at the operative area within the thermoelectric insulative shield 35.

It will be immediately apparent to those skilled in the art that the electroresectroscope apparatus and method as set forth in the foregoing specification substantially simplifies laparoscopic tubal sterilization. It is equally apparent that the electrosurgery as accomplished by the preferred embodiment of the electroresectroscope in a shielded environment with localized application of electrical energy prevents thermal burns to the patient, provides a greater degree of safety for the surgeon, and otherwise achieves the objectives previously set forth. Various changes and modifications to the particular apparatus herein shown are anticipated. Particular changes are foreseen in size and shape of devices, materials of construction, electrical energy requirements with regard to the resistance and desired output of the heating element, and other similar specifics which do not detract from the scope and intent of the invention.

Having fully described and disclosed the present invention and the preferred embodiment thereof in such clear and concise terms as to enable those skilled in the art to understand and practice the same, the invention claimed is:

1. A resectroscope adapted for use during laparoscopic sterilization of a Fallopian tube, said resectroscope comprising:
   a. an elongate tubular sheath having forward and rearward opening ends, at least the forward end thereof being electrically insulative;
   b. grasping means slidably carried within said tubular sheath for extending from the forward end thereof to engage a Fallopian tube and retract a section thereof within the interior of the forward end of said sheath; and
   c. means for subjecting said section of said Fallopian tube located interior of said forward opening to conditions sufficient for electroresection and electrocoagulation.

2. The resectroscope of claim 1 wherein said grasping means comprises:
   a. an elongate member having a forward end and a rearward end and dimensioned to be slidably carried within said tubular sheath; and
   b. a hook-shaped electrical resistance heating element carried proximate the forward end of said elongate member, said elongate member and said tubular sheath having means proximate the rearward ends thereof for movement relative to one another between a position in which said heating element extends from the forward opening of said tubular sheath and a position in which said heating element is retracted to a position interior of said forward opening.

3. The electroscope of claim 2, wherein said insulative forward end comprises a disposable thermoelectric insulating forward end portion detachably secured to said tubular sheath.

4. The method of performing a laparoscopic tubal sterilization, including the steps of:
   a. extending a hook-shaped electrical resistance element from a thermoelectric insulating tubular sheath;
   b. engaging a Fallopian tube with said resistance element to form a doubled length of said Fallopian tube;
   c. retracting said resistance element and a portion of said doubled Fallopian tube within said tubular sheath; and
   d. applying electrical energy to said resistance element for electroresection of said Fallopian tube to produce two fulgurated ends thereof and concurrent electrocoagulation of said fulgurated ends within said sheath.

5. A resectroscope kit for use during laparoscopic tubal sterilization for initial surgical entry into the peritoneal cavity and for subsequent controlled shielded electroresection and electrocoagulation of a Fallopian tube, said resectroscope kit comprising:
   a. an elongate tubular sheath having an open forward probe used end and an open rearward end and being thermoelectrically insulative at least in the area of the probe used end;
   b. a first elongate stylet slidably received within said sheath and including a surgically incisive tip extending beyond the forward end of said sheath, said tip acting as a guide for surgical entry of said sheath into the peritoneal cavity;
   c. a second elongate stylet slidably receivable within said sheath and adapted to replace said first stylet and having forward and rearward ends;
   d. a hook-shaped electrical resistance heating element extending from the forward end of said second stylet and extensible and retractable relative the forward end of said sheath in response to sliding movement of said second stylet,
   said hook-shaped element engageable with a Fallopian tube when extended and subsequently positioning the engaged section of the Fallopian tube within the insulated area of said sheath when retracted; and
   e. means for selectively transmitting a predetermined electrical energy impulse to said hook-shaped element for electroresection and electroagulation of the Fallopian tube within the insulated area of said sheath.

* * * * *